(12) United States Patent
Lin et al.

(10) Patent No.: US 6,534,002 B1
(45) Date of Patent: *Mar. 18, 2003

(54) FLOW OF FLUID THROUGH A LUMEN DEVICE FROM SMALLER-CALIBER END TO LARGER-CALIBER END

(75) Inventors: Szu-Min Lin, Laguna Hills, CA (US); Paul Jacobs, Trabuco Canyon, CA (US)

(73) Assignee: Ethicon, Inc., New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/223,119

(22) Filed: Dec. 30, 1998

(51) Int. Cl.$^7$ .............................. A61L 2/00; A61L 9/00
(52) U.S. Cl. ................... 422/28; 422/32; 422/33
(58) Field of Search ..................... 422/28–33, 40, 422/292, 294, 295, 298, 297, 300

(56) References Cited

U.S. PATENT DOCUMENTS

| | | |
|---|---|---|
| 3,814,901 A | 6/1974 | Morhack |
| 4,203,943 A | 5/1980 | Gillis et al. |
| 4,321,232 A | 3/1982 | Bithell |
| 4,337,223 A | 6/1982 | Kaye |
| 4,380,530 A | 4/1983 | Kaye |
| 4,410,492 A | 10/1983 | Kaye |
| 4,526,622 A | 7/1985 | Takamura et al. |
| 4,526,623 A * | 7/1985 | Ishii et al. ............ 134/21 |
| 4,576,650 A | 3/1986 | Yabe et al. |
| 4,576,792 A | 3/1986 | Martensson |
| 4,579,597 A | 4/1986 | Sasa et al. |
| 4,579,598 A | 4/1986 | Sasa et al. |
| 4,731,222 A | 3/1988 | Kralovic et al. |
| 4,744,951 A | 5/1988 | Cummings et al. |
| 4,756,882 A | 7/1988 | Jacobs et al. |
| 4,892,706 A | 1/1990 | Kralovic et al. |
| 4,937,046 A | 6/1990 | Andersen et al. |
| 4,943,414 A | 7/1990 | Jacos et al. |

(List continued on next page.)

FOREIGN PATENT DOCUMENTS

| | | |
|---|---|---|
| DE | 3416743 A1 | 7/1985 |
| DE | 3819257 C1 | 6/1988 |
| EP | 0 923 951 A2 | 12/1998 |
| WO | WO 9724147 | 7/1997 |

*Primary Examiner*—Robert J. Warden, Sr.
*Assistant Examiner*—Monzer R. Chorbaji
(74) *Attorney, Agent, or Firm*—Knobbe, Martens, Olson & Bear, LLP

(57) ABSTRACT

Disclosed is a method of cleaning endoscopes within a container, wherein fluid flows from inside the container through the endoscope channels, predominantly in one direction, from the smaller-caliber end of an endoscope channel, or lumen, to the larger-caliber end. This method prevents the lodgment of particulate matter and human tissue in the smaller-caliber end of endoscope channels, and it allows fluid to flow through the entire length of all endoscope channels, to permit debris to exit the channels.

24 Claims, 2 Drawing Sheets

U.S. PATENT DOCUMENTS

| | | | |
|---|---|---|---|
| 4,956,145 A | | 9/1990 | Cummings et al. |
| 5,017,241 A | | 5/1991 | Ryan |
| 5,037,623 A | | 8/1991 | Schneider et al. |
| 5,077,008 A | | 12/1991 | Kralovic et al. |
| 5,091,343 A | | 2/1992 | Schneider et al. |
| 5,093,079 A | * | 3/1992 | Bakaitis et al. ............... 422/28 |
| 5,114,596 A | | 5/1992 | Laterra |
| 5,116,575 A | | 5/1992 | Badertscher et al. |
| 5,186,893 A | | 2/1993 | Moulton et al. |
| 5,209,909 A | | 5/1993 | Siegal et al. |
| 5,217,698 A | | 6/1993 | Siegel et al. |
| 5,225,160 A | | 7/1993 | Sanford et al. |
| 5,260,021 A | | 11/1993 | Zeleznick |
| 5,266,275 A | | 11/1993 | Faddis |
| 5,279,799 A | | 1/1994 | Moser |
| 5,288,467 A | * | 2/1994 | Biermaier ................... 422/116 |
| 5,310,524 A | | 5/1994 | Campbell et al. |
| 5,348,711 A | | 9/1994 | Johnson et al. |
| 5,350,563 A | | 9/1994 | Kralovic et al. |
| 5,374,394 A | | 12/1994 | Kralovic |
| 5,391,360 A | | 2/1995 | Kochte et al. |
| 5,407,648 A | | 4/1995 | Allen et al. |
| 5,407,685 A | | 4/1995 | Malchesky et al. |
| 5,413,758 A | * | 5/1995 | Caputo et al. ................ 422/22 |
| 5,441,707 A | | 8/1995 | Lewis et al. |
| 5,443,801 A | * | 8/1995 | Langford .................... 422/294 |
| 5,445,792 A | | 8/1995 | Rickloff et al. |
| 5,492,671 A | | 2/1996 | Krafft |
| 5,494,530 A | | 2/1996 | Graf |
| 5,505,218 A | | 4/1996 | Steinhauser et al. |
| 5,508,009 A | | 4/1996 | Rickloff et al. |
| 5,527,508 A | | 6/1996 | Childers et al. |
| 5,534,221 A | | 7/1996 | Hillebrenner et al. |
| 5,540,901 A | | 7/1996 | Riley |
| 5,552,115 A | | 9/1996 | Malchesky |
| 5,556,607 A | | 9/1996 | Childers et al. |
| 5,580,530 A | | 12/1996 | Kowatsch et al. |
| 5,599,512 A | * | 2/1997 | Latulippe et al. ........... 422/300 |
| 5,609,821 A | | 3/1997 | Grimberg et al. |
| 5,711,921 A | * | 1/1998 | Langford .................... 422/292 |
| 5,738,824 A | * | 4/1998 | Pfeifer .......................... 422/3 |
| 5,784,468 A | | 7/1998 | Klayman |
| 5,851,485 A | * | 12/1998 | Lin et al. ...................... 422/33 |
| 6,066,294 A | * | 5/2000 | Lin et al. |
| 6,083,458 A | * | 7/2000 | Lin et al. |
| 6,187,266 B1 | * | 2/2001 | Lin et al. |
| 6,312,645 B1 | * | 11/2001 | Lin et al. |

* cited by examiner

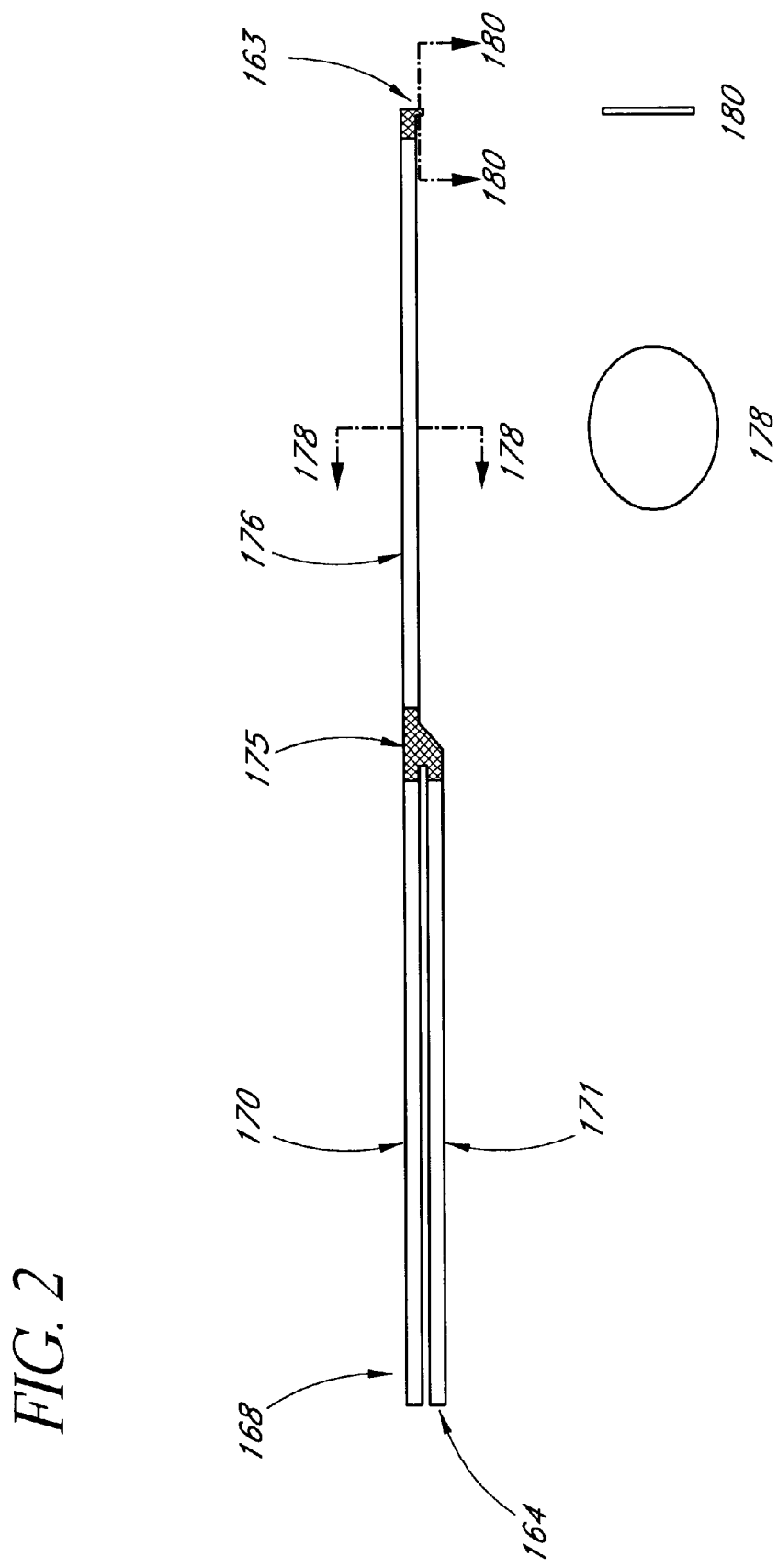

FLOW OF FLUID THROUGH A LUMEN DEVICE FROM SMALLER-CALIBER END TO LARGER-CALIBER END

BACKGROUND OF THE INVENTION

This invention relates to systems and processes for cleaning, disinfecting, and sterilizing medical devices that have inner channels or chambers, particularly endoscopes.

Medical instruments have traditionally been sterilized or disinfected using either heat, such as is provided by steam, or a chemical in liquid, gas, or vapor state. Prior to sterilization or disinfection, the instruments to be treated are usually first cleaned. After sterilization or disinfection with a liquid chemical germicide, sterile water is used to rinse the instruments, and then the instruments are dried.

Endoscopes are flexible or rigid tubes having a multiplicity of endings. Within a any given endoscope, there may be multiple channels, or lumens. These channels serve distinct purposes. They allow for suction; the placement of instruments for biopsy, fulguration, or electrocautery by a physician; or the flow of liquid, air, or carbon dioxide ($CO_2$) gas into a body cavity. Merely soaking endoscopes in a sterilant or detergent is unacceptable, since numerous pockets exist within the tubing where the sterilant or detergent cannot reach effectively. This leaves areas of contamination within the endoscope. With the prevalence of contagious diseases, such as hepatitis B, hepatitis C, and human immunodeficiency virus (HIV), sterilization or disposal of medical instruments is critical.

After use, endoscopes are sometimes discarded due to the difficulty in cleaning and sterilizing the endoscope before subsequent use. Endoscopes are very expensive, and their disposal after one use is wasteful because the structural and mechanical integrity of the endoscope has not been compromised, only its cleanness.

Traditionally, the channels inside endoscopes have been cleaned by attaching the ends of the channels to connectors and then pumping cleaning solution through the channels. U.S. Pat. No. 4,579,598 to Sasa, et al., discloses one such method of cleaning endoscopes using connectors. One problem with using connectors is that the interface between the connector and the endoscope is not exposed to the flow of cleaning solution. As a result, these interfaces are not fully cleaned. Another problem with cleaning systems that use connectors is that only the endoscope channels can be cleaned, and not the exterior surface of the endoscope. Furthermore, some endoscopes, such as those used for endoscopic surgery, need not only to be cleaned but also sterilized. Traditional systems that use connectors for cleaning endoscopes do not sterilize the endoscope.

One system for cleaning both the inside channels and the outside surfaces of an endoscope involves placing the endoscope into a container, and then allowing fluid that has been introduced into the container to flow around the endoscope and through its channels. U.S. Pat. No. 5,711,921 to Langford discloses a "surging" method for cleaning endoscopes in this fashion. This method involves placing an endoscope into a container, which is divided into two chambers by a partition. Fluid flows back and forth, or surges, between these chambers by alternating the pressure in the chambers, such that while fluid pressure increases in the first chamber, fluid pressure decreases within the second chamber, and vice versa.

One significant problem with this surging mechanism for cleaning endoscopes results from the fact that endoscope channels often have different diameters at their opposite ends. As fluid flows from the larger-caliber end of an endoscope channel to the smaller-caliber end, particulate matter and human tissue, secretions, and excrement can become lodged in the smaller-caliber end and extremely difficult to extract.

Another problem with the surging mechanism results from the frequent change in directional flow of fluid through the channels of an endoscope. In cleaning an endoscope, debris must travel a long distance, sometimes more than 150 cm, to traverse the length of the endoscope before the debris can exit the endoscope. In surging methods of cleaning endoscopes, some fluid, debris, and air pockets may move back and forth within the endoscope channel, but never travel far enough to exit the channel before the next directional shift in flow occurs. Thus, some debris and air pockets can remain trapped in the central portion of an endoscope channel with the surging method of cleaning.

Thus, there remains a need for a method of cleaning endoscopes by flowing fluid through the endoscope channels that avoids the lodgment of material in the smaller-caliber end of endoscope channels, such as occurs with the back-and-forth flow of fluid seen with surging mechanisms.

SUMMARY OF THE INVENTION

The present invention discloses a method of cleaning an endoscope within a container, wherein fluid flows predominantly or only in one direction, from the smaller-caliber end of an endoscope channel, or lumen, to the larger caliber end. This method prevents the lodgment of particulate matter and human tissue in the smaller-caliber end of endoscope channels, and it allows fluid to flow through the entire length of all endoscope channels, to permit debris to exit the channels.

In one aspect of the present invention there is provided a method for cleaning or sterilizing a tubular device having a lumen with a smaller-caliber open end and a larger-caliber open end, and an inner surface and an outer surface. This method comprises the acts of placing the device into a container having at least one interface with an adjustable opening, which interface separates the container into two or more compartments. The device is placed across the interface with one open end of the endoscope in one of the compartments and another open end of the device in another compartment. Cleaning solution, rinse solution or chemical germicide is introduced into the container, and a flow of this fluid is generated from inside the container through the inner channel of the tubular device, from the smaller-caliber end to the larger-caliber end, to clean or sterilize the inner surface of the tubular device.

In a further aspect of the present invention, a flow of cleaning solution, rinse solution, or chemical germicide is generated from inside one of the compartments to another of the compartments, around the outer surface of the tubular device, to clean or sterilize the outer surface of the device. In another aspect of the invention, one or more of the preceding acts are repeated. In a further aspect of the present invention, the interface within the container is adjusted by adjusting an adjustable aperture or seal that varies the relative amount of exposure of the inner surface and the outer surface of the tubular device to cleaning solution, chemical germicide or rinse solution.

In another embodiment of the present invention, the method is used to treat a nonmovant device in the container.

In a further aspect of the present invention, sterilization of the tubular device is conducted under a reduced pressure.

After cleaning the tubular device, a predetermined amount of chemical germicide may be left in the container, and the retained chemical germicide is vaporized under reduced pressure, in order to sterilize the device. In an alternative embodiment of the method, the sterilization is conducted by reducing the pressure in the container to a first predetermined pressure, followed by further reducing the first pressure to a predetermined second pressure. In an alternative embodiment of the method, the sterilization is conducted at a controlled pump-down rate.

In a further aspect of the present method, the container is placed into or attached to a vacuum system, for applying reduced pressure to the container. The container is then removed or detached from the vacuum system after the device is sterilized. In one embodiment, the device maintains sterility in the container after the device is sterilized. The method further comprises drying the device in the container after sterilization.

In one embodiment of the invention, the container comprises flexible material. This flexible material can be gas-permeable and liquid-impermeable. In another embodiment, the container comprises gas-impermeable material. In another aspect of the present method, the container has one or more openings, or ports, to permit influx or efflux of fluid for purposes of cleaning or sterilizing the device. In one embodiment, the interface within the container has at least two independently controllable apertures for holding and sealing the device. In a further aspect of the invention, the act of adjusting the interface comprises opening one of the two or more apertures while closing the other apertures, so that the areas on the outer and inner surfaces of the device are alternately exposed to the cleaning solution, rinse solution or chemical germicide.

In a further aspect of the method, the flow of fluid through the lumen of the tubular device is generated by applying a pressure higher than atmospheric pressure at one end of the lumen, or by applying a vacuum to one end of the lumen device.

In a further aspect of the invention, the interface in the container has separately controllable and movable contact points, and the adjusting act comprises controlling the contact points so that a different portion of the contact points is made in contact with the device alternately.

In a further aspect of the invention, the interface forms a seal around the device selected from the group consisting of a gas-type seal, a tight-fitting seal, or a loose-fitting seal.

BRIEF DESCRIPTION OF THE DRAWINGS

FIG. 2 is a side view of two endoscope channels, which connect to form one common channel.

DETAILED DESCRIPTION OF THE PREFERRED EMBODIMENTS

Figure 1:
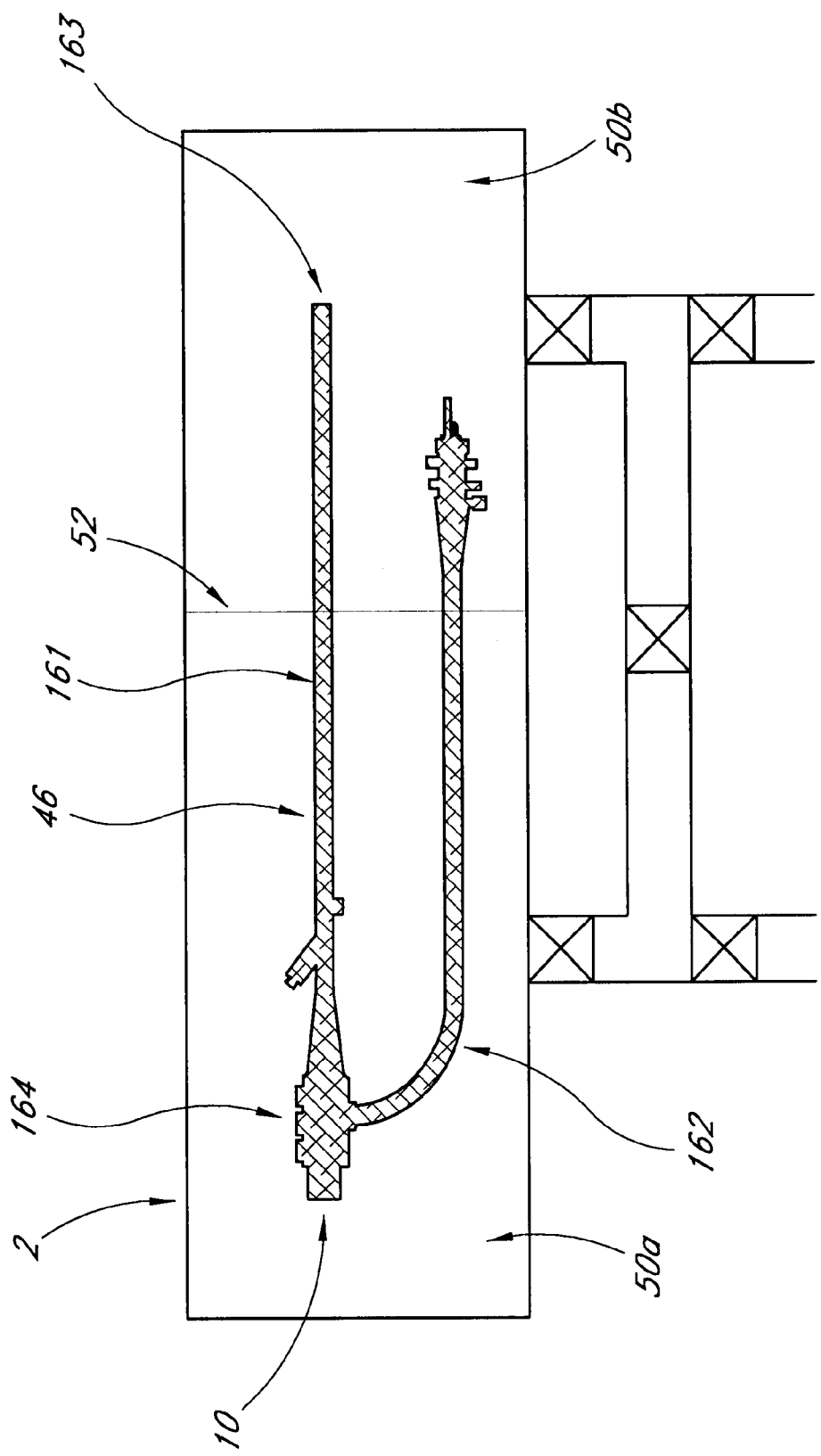
FIG. 1 is a side view of a container containing an endoscope.

Several preferred embodiments of the present invention will be described with reference to the accompanying drawings. Although the description below is primarily directed to the cleaning and sterilizing of endoscopes, other devices with inner channels or chambers can be cleaned or sterilized with the present invention, as will be readily apparent to one of skill in the art in view of the disclosure herein.

FIG. 1 discloses an endoscope 46 inside a container 2. In one embodiment, the container is divided into two chambers, 50a and 50b, by an interface 52. This interface comprises at least one adjustable opening. In other embodiments, the container can be divided into more than two chambers (50a and 50b) by the addition of extra interfaces 52. In a further aspect of the invention, the interface forms a seal around the device selected from the group consisting of a gas-type seal, a tight-fitting seal, or a loose-fitting seal.

Positioned in the container 2, the endoscope 46 traverses the interface 52. The endoscope 2 typically comprises a control head 10, from which the endoscopist can press buttons or adjust other controls (not shown) in order to change the flow of air, water, and suction through the endoscope's channels (not shown). The endoscope 2 typically also comprises two main arms: an insertion tube 161, which is inserted into a patient's body, and an umbilical cord 162 (sometimes also called a "universal cord"), which attaches to machine (not shown) that supplies air, water, and suction to the endoscope channels.

A sanitizing solution, herein defined as a cleaning solution, rinse solution, and/or chemical germicide, is introduced into the container 2, and a flow of this fluid is generated from inside the container through the inner channel of the endoscope, from the smaller-caliber end 163 to the larger-caliber end 164, to clean or sterilize the inner channel of the endoscope.

In a further aspect of the present invention, a flow of cleaning solution, rinse solution, or chemical germicide is generated from inside one (50b) of the compartments to another (50a) of the compartments, around the outer surface of the endoscope 46, to clean or sterilize the outer surface of the endoscope 46. In another aspect of the present invention, one or more of the preceding acts are repeated. In a further aspect of the invention, the interface 52 within the container 2 is adjusted by adjusting an adjustable aperture or seal that varies the relative amount of exposure of the inner channel and the outer surface of the endoscope 46 to cleaning solution, chemical germicide or rinse solution.

In a further aspect of the present invention, sterilization of the endoscope 46 is conducted under a reduced pressure. After cleaning the endoscope 46, a predetermined amount of chemical germicide may be left in the container 2. This process of leaving some chemical germicide in the container 2 is sometimes referred to as "pretreatment" by those skilled in the art, and this process of pretreatment is included in the definition of "sterilization" as the term is used herein. The retained chemical germicide is vaporized under reduced pressure in order to sterilize the device. In an alternative embodiment of the method, the sterilization is conducted by reducing the pressure in the container 2 to a first predetermined pressure, followed by further reducing the first pressure to a predetermined second pressure. In a further embodiment of the method, the sterilization is conducted at a controlled pump-down rate, as described below.

In a further aspect of the present method, the container is placed into or attached to a vacuum system, for applying reduced pressure to the container. The container is then removed or detached from the vacuum system after the device is sterilized. In one embodiment, the device maintains sterility in the container after the device is sterilized. The method further comprises drying the device in the container after sterilization.

In one embodiment of the invention, the container 2 comprises flexible material. This flexible material can be gas-permeable and liquid-impermeable. In another embodiment, the container comprises gas-impermeable material. In another aspect of the present method, the container 2 has one or more openings, or ports, to permit influx or efflux of fluid for purposes of cleaning or sterilizing the device. In one embodiment, the interface 52 within the container 2 has at least two independently controllable apertures for holding and sealing the device. In a further aspect of the invention, the act of adjusting the interface 52 comprises opening one of the two or more apertures while closing the other apertures, so that the areas on the outer and inner surfaces of the endoscope 46 are alternately exposed to the cleaning solution, rinse solution or chemical germicide.

In a further aspect of the method, the flow of fluid through the channel of the endoscope 46 is generated by applying a pressure higher than atmospheric pressure at one end of the lumen, or by applying a vacuum to one end of the lumen device.

In a further aspect of the invention, the interface 52 in the container 2 has separately controllable and movable contact points, and the adjusting act comprises controlling the contact points so that a different portion of the contact points is made in contact with the endoscope 46 alternately.

FIG. 2 discloses a set of channels 168 that exist within an endoscope. While FIG. 2 is exemplary, there can exist a wide range of numbers and configurations of endoscope channels within a given endoscope. Although the description below is primarily directed to the transmission of air and water through endoscope channels, channels that are used for other purposes can be used in conjunction with the present invention, as will be readily apparent to one of skill in the art in view of the disclosure herein. Thus, the present invention can also be used to clean and sterilize endoscope channels that allow for the placement of instruments for biopsy, fulguration, or electrocautery; or that allow transmission of the flow of carbon dioxide ($CO_2$) or other gas.

During an endoscopic procedure, air can be transmitted through channel 170, and water can be transmitted through channel 171, or vice versa. During an endoscopic procedure, the direction of the flow of air and water occurs from a larger-caliber end 164 of the endoscope channels (170 and 171) to the smaller-caliber end 163 of the channel 176. The air channel 170 and the water channel 171 converge at a connector 175. During an endoscopic procedure, the flow of air and water continues from the air channel 170 and the water channel 171 through the connector 175, and through a common channel 176 toward a small opening 180 at the distal, smaller-caliber end 163 of the common channel 176.

The cross-sectional diameter of the common channel typically narrows greatly (e.g., tenfold) in going from the midsection 178 of the common channel 176 to the small opening 180 of the common channel 176. Typical cross-sectional diameters of the common channel 176 are approximately 1 mm at the midsection 178 and approximately 0.1 mm×1 mm at the small, rectangular opening 180 of the common channel 176. Because of this narrowing, methods of cleaning endoscopes that utilize the flow of fluid from the larger-caliber end 164 to the smaller-caliber end 163 of an endoscope 46 frequently cause debris to accumulate at the smaller-caliber end 163 of an endoscope channel 176, sometimes leading to obstruction of the small opening 180.

In the present method, fluid flows predominantly or only from the smaller-caliber end 163 to the larger-caliber end 164 of the endoscope channel 176, thus preventing lodgment of debris in the smaller-caliber end 163 of the endoscope channel 176.

Method Based on Controlled Pump-Down Rate

The cleaning/sterilizing process of the present invention can also be carried out in cooperation with a controlled pump-down method without relying on a diffusion-restricted environment.

Effective sterilization results similar to those created in diffusion-restricted environments can be created through controlling the evacuation rate of a chamber or container in which devices to be sterilized are placed. Thus, in one embodiment of the present invention, this controlled pump-down rate method comprises the acts of contacting the device with a liquid sterilant at a first pressure; draining excess liquid sterilant to retain a predetermined amount of the sterilant, and decreasing the pressure of the chamber to a second pressure below the vapor pressure of the liquid sterilant in which at least a portion of the decrease in pressure below the vapor pressure of the liquid sterilant occurs at a pump-down rate of less than 0.8 liters per second, calculated based on the time required to evacuate the chamber from atmospheric pressure to 20 torr when the chamber is empty and dry, i.e. when the chamber has neither devices to be sterilized nor a visible quantity of liquid within it. According to one aspect of this preferred embodiment, at least the decrease in pressure below about two times the vapor pressure of the liquid sterilant occurs at a pump-down rate of less than 0.8 liters per second. According to another embodiment, the decrease in pressure below about four times the vapor pressure of the liquid sterilant occurs at a pump-down rate of less than 0.8 liters per second. Preferably, the pump-down rate is 0.6 liters per second or less; more preferably, 0.4 liters per second or less; and most preferably, 0.2 liters per second or less. Advantageously, the first pressure is atmospheric pressure. Preferably, the liquid sterilant is hydrogen peroxide. The hydrogen peroxide usually is a solution as used in the art, preferably it is a 3–60% solution. The device can be a lumen or non-lumen medical instrument.

The present invention can also incorporate a method for sterilizing a device comprising the acts of (a) contacting the device with liquid sterilant at a first pressure; (b) retaining a predetermined amount of the liquid sterilant in the container; (c) pumping down the container or chamber to a second pressure which is lower than the first pressure at a first rate; and (d) pumping down the container or chamber to a third pressure which is lower than the second pressure, wherein at least a portion of the pumping down to the third pressure is at a second rate which is slower than the first rate. The pump-down rate either above and/or below the second pressure can be constant or variable. In certain embodiments, the pump-down rate either above and/or below the second pressure is reduced in stepwise fashion. Preferably, the second pressure is greater than or equal to about the vapor pressure of the liquid sterilant; more preferably, the second pressure is greater than or equal to about two times the vapor pressure of the liquid sterilant; most preferably, the second pressure is greater than or equal to about four times the vapor pressure of the liquid sterilant. Advantageously, the pump-down rate in act (d) is 0.8 liters/sec or less; more advantageously 0.6 liters/sec or less; even more advantageously 0.4 liters/sec or less; and most advantageously 0.2 liters/sec or less, calculated based on the time required to evacuate the chamber from atmospheric pressure to 20 torr under empty and dry conditions. Preferably, the liquid sterilant is hydrogen peroxide. In another embodiment, the device is a medical instrument having a lumen. Preferably, the pumping down of act (c) reduces the pressure to less than about three times, more preferably to less than about two times, the vapor pressure of the liquid sterilant.

Another suitable method includes contacting the device with liquid sterilant, retaining a predetermined amount of the liquid sterilant in the container, and reducing the pressure of the chamber while regulating the pump-down rate so as to control the evaporation rate of sterilant in the chamber. In any of the methods described above, the contacting act may comprise application of liquid or condensed vapor. These methods described above may additionally comprise further evacuating the chamber to remove residual sterilant. Further, these methods described above may additionally comprise exposing the device to plasma to remove residual sterilant or enhance sterilization efficacy. The contacting act in these methods can be either by direct or indirect contacting. As stated herein, indirect contacting involves introducing sterilant into the chamber without directly contacting the device to be sterilized.

A. Two-Step Pump-Down Method

A two-step pump-down sterilization method can also be used in cooperation with the cleaning/sterilizing process of the present invention. This method comprises the steps of contacting a device with liquid sterilant; draining excess liquid sterilant to retain a predetermined amount of the sterilant; bringing the pressure of the chamber to a first pressure range at which the liquid sterilant is vaporized from non-diffusion restricted area of the device to sterilize the non-diffusion restricted area; bringing the pressure of the chamber to a second pressure range at which the liquid sterilant is vaporized from diffusion restricted area of the device to sterilize the diffusion restricted area, wherein the minimum pressure in the second pressure range is lower than the maximum pressure in the first pressure range.

Preferably, the first pressure range is from 20 to 760 torr; more preferably, the first pressure range is 20 to 80 torr; most preferably, the first pressure range is 40–50 torr. Advantageously, the second pressure range is 1–30 torr; more advantageously, the second pressure range is 5–10 torr. In one preferred embodiment, the device includes a diffusion-restricted environment. Preferably, the device is a medical instrument with a lumen. Advantageously, the sterilant is hydrogen peroxide. According to another aspect of this preferred embodiment, the chamber is at a set temperature and wherein the first pressure is preferably lower than the vapor pressure of the sterilant at the set temperature. Preferably, the pressure of the chamber is maintained constant at the first pressure for a time period sufficient to sterilize the non-diffusion-restricted area. Advantageously, the pressure of the chamber is maintained constant at the second pressure for a time period sufficient to sterilize the diffusion-restricted area. The pressure of the chamber may be permitted to increase after reaching the first or second pressure range as a result of vaporization of the sterilant within the chamber. Alternatively, the pressure of the chamber is permitted to decrease after reaching the first or second pressure through pumping of the chamber at a rate slower than used to decrease the pressure between the first and second pressure ranges. Preferably, the contacting step is with liquid, condensed vapor, or mist. The method can also include the steps of bringing the pressure to a third pressure lower than the second pressure to remove residual sterilant and/or exposing the device to plasma to remove residual sterilant or enhance sterilization efficacy.

Method Involving Direct Flow Through a Lumen of the Device to Be Sterilized

The flow of a germicide (solution or vapor) or any cleaning solution through a lumen of a medical device is driven by a pressure drop between two open ends of the lumen. The pressure drop can be generated by applying either a vacuum or a high pressure at one end. By generating a forced flow through a pressure differential other than relying on diffusion, the sterilization rate is significantly increased and less time is needed for a sterilization cycle.

The two ends of the lumen must be exposed to a pressure differential. This is achieved in the present invention by placing a sealable interface that separates two chambers within the container. An adjustable opening is provided in the interface and the lumen device to be sterilized is placed through the opening so that the lumen serves as a flow path between the two chambers.

The opening can be constructed in several ways. One way to achieve this is with a camera-shutter approach employing an iris diaphragm, such as a precision iris diaphragm from Edmund Scientific. An optional spring can be used to secure the closure of the shutter. Also commercially available is Syntron Iris Flow Control Valve manufactured by FMC Corporation. This Iris Valve has a sleeve made of Teflon or other synthetic material defining an aperture. By rotating two ends of the sleeve relative to each other, the aperture can be reduced or increased. Iris diaphragm valves from Kemutec Inc. are also commercially available which can be automatically controlled. Another example is the AirGripper and AirPicker manufactured by Firestone Industrial Products Company. Another way to construct an openable and closeable opening is to employ two plates. Two edges of the two plates form a gap that can be adjusted by moving the two plates relative to each other. One or more lumen devices are placed through the gap formed between the two plates and the two plates are moved together to form a seal around the lumen devices. The edges of the two plates forming the gap can be equipped with compressible material or expandable material. When expandable material is used, a fluid source can be provided to expand the expandable material. Optionally, a porous material like a sponge or air permeable material may be utilized on the edges. In this case some sterilant can diffuse through the porous material to the outer surface of the lumen device occluded by the closed opening. However, most of the sterilant flows through the lumen device. Another usable interface is a hole or a slot, the hole or slot is equipped with gas or liquid inflatable material so that by inflating the inflatable material on the hole or the slot the opening is reduced and the lumen device is held and sealed. Still another option is to place a compressible material on top of an expandable or inflatable material so as to facilitate the sealing around the lumen device.

The closing and opening movement of the opening can be controlled mechanically or electronically with any conventional mechanism. The degree of opening is adjustable. Thus, it can be sealed to a different degree between the opening and the lumen device depending on the desired purpose. For example, the opening can form a gas-tight seal, a tight-fitting seal, or a loose-fitting seal around the lumen device. As used herein, a gas-tight seal refers to a seal that substantially stops liquid and gas flow through the contact area between the opening and the lumen device surface. When a gas-tight seal is employed, preferably the device to be sterilized is first pre-cleaned so that the occluded area by the seal is cleaned before the gas-tight seal is formed. A loose-fitting seal allows both liquid and gas to flow through the gap between the opening and the lumen device surface, and in the meantime is able to maintain a pressure drop across the interface enough to generate a flow through the lumen. A tight-fitting seal allows gas and liquid to penetrate to the contact area between the opening and the lumen device surface by diffusion. For example, a tight-fitting seal can be formed with porous material or textures provided on the contact surface of the opening. Thus, with a gas-tight seal, the device is held tightly by the closed opening. In the tight-fitting seal, the closed opening also holds the device in position. In the case of a loose-fitting seal, the device can move relative to the opening, but is not flashed away. The interface can be made openable, closeable, and removable, and may have more than one opening. In order to promote sterilization efficiency, all the sterilization apparatuses of the present invention can be further equipped with a heater and/or a plasma.

The present invention has been described above. Many modifications and variations of the cleaning and sterilizing processes and the apparatus used in such processes may be made without departing substantially from the spirit and scope of the present invention. Accordingly, it should be clearly understood that the form of the invention described and illustrated herein is exemplary only, and is not intended as a limitation on the scope.

What is claimed is:

1. A method for cleaning or sterilizing a device having a lumen with at least a smaller-caliber open end and a larger-caliber open end, and an inner surface and outer surface, said method comprising the acts of:
    a) providing a container having at least one interface with an opening, said interface separating said container into two or more compartments;
    b) placing said device across said interface with a smaller-caliber open end of said device in one of said compartments and a larger-caliber open end in another of said compartment;
    c) introducing a sanitizing solution into said container; and
    d) generating a flow of said sanitizing solution from inside said container through said lumen in predominantly one direction, from the smaller-caliber end to the larger-caliber end, to clean or sterilize the inner surface of said device.

2. A method of claim 1, additionally comprising the act of generating a flow of sanitizing solution from inside one of said compartments to another of said compartments, around the outer surface of said device, to clean or sterilize the outer surface of said device.

3. A method of claim 2, wherein one or more of said acts are repeated.

4. A method of claim 2, further comprising the act of adjusting an adjustable aperture or seal that varies the relative amount of exposure of the inner surface and the outer surface of said device to sanitizing solution.

5. A method of claim 1, further comprising the act of adjusting an adjustable aperture or seal that varies the relative amount of exposure of the inner surface and the outer surface of said device to sanitizing solution.

6. A method of claim 1, further comprising cleaning or sterilizing a non-lumen device in said container.

7. A method of claim 1, wherein sterilizing is conducted under a reduced pressure.

8. A method of claim 7, further comprising retaining a chemical germicide in said container and vaporizing the retained chemical germicide to sterilize said device under reduced pressure after act d).

9. A method of claim 8, wherein the sterilizing is conducted by reducing pressure to a first predetermined pressure, followed by further reducing said first pressure to a predetermined second pressure.

10. A method of claim 8, wherein the sterilizing is conducted at controlled pump-down rate.

11. A method of claim 7, further comprising the act of removably attaching said container to a vacuum system for applying reduced pressure to said container, and detaching said container after the device is sterilized.

12. A method of claim 1, wherein the sterility of said device is maintained in the container after said device is sterilized.

13. A method of claim 1, further comprising the act of drying said device after sterilization.

14. A method of claim 1, wherein said container comprises flexible material or materials.

15. A method of claim 1, wherein said container comprises gas-perneable and liquid-impermeable material.

16. A method of claim 15, further comprising the act of exposing container, with said device present inside it, to a reduced pressure in a vacuum chamber.

17. A method of claim 1, wherein said container comprises gas-impermeable material.

18. A method of claim 1, wherein said container has one or more openings, or ports, to permit influx or efflux of fluid for purposes of cleaning or sterilizing said device.

19. A method of claim 1, wherein, along its passage, said interface has at least two independently controllable apertures for holding and sealing said device.

20. A method of claim 19, wherein the act of adjusting said interface comprises opening one of said two or more apertures while closing the other of said aperture(s) so that the areas on the outer and inner surfaces of said device are alternately exposed to said sanitizing solution.

21. A method of claim 1, wherein the flow through said lumen is generated by applying a pressure higher than atmospheric pressure at one end of said lumen, or by applying vacuum to one end of said lumen device.

22. A method of claim 1, wherein said interface has separately controllable and movable contact points, and further comprising the act of adjusting said contact points so that a different portion of said contact points is made in contact with the device alternately.

23. A method of claim 1, wherein the interface forms a seal around said device selected from the group consisting of a gas-tight seal, a tight-fitting seal, and a loose-fitting seal.

24. A method of claim 1, wherein said device is an endoscope.

* * * * *